United States Patent

Mine et al.

[11] Patent Number: 5,972,243
[45] Date of Patent: Oct. 26, 1999

[54] FERRIELECTRIC LIQUID CRYSTAL COMPOUND

[75] Inventors: Takakiyo Mine; Masahiro Johno; Tomoyuki Yui; Yasue Yoshioka, all of Tsukuba, Japan

[73] Assignee: Mitsubishi Gas Chemical Company, Inc., Tokyo, Japan

[21] Appl. No.: 09/121,123

[22] Filed: Jul. 23, 1998

[30] Foreign Application Priority Data

Jul. 23, 1997 [JP] Japan ..................... 9-197231

[51] Int. Cl.⁶ .................. C09K 19/12; C07C 69/76; C07C 25/13
[52] U.S. Cl. ................ 252/299.65; 252/299.64; 560/65; 560/83; 570/129; 570/130
[58] Field of Search ............ 252/299.65, 299.64, 252/299.67; 570/129, 130; 560/65, 83; 136/254

[56] References Cited

U.S. PATENT DOCUMENTS

| | | | |
|---|---|---|---|
| 4,780,242 | 10/1988 | Miyazawa et al. | 252/299.65 |
| 5,076,962 | 12/1991 | Furukawa et al. | 252/299.65 |
| 5,167,855 | 12/1992 | Wand et al. | 252/299.01 |
| 5,312,564 | 5/1994 | Miyazawa et al. | 252/299.65 |

FOREIGN PATENT DOCUMENTS

| | | |
|---|---|---|
| 0342046 | 11/1989 | European Pat. Off. |
| 0450595 | 10/1991 | European Pat. Off. |
| 0582468 | 2/1994 | European Pat. Off. |
| 5150257 | 6/1993 | Japan . |
| 5249502 | 9/1993 | Japan . |
| 6-95080 | 4/1994 | Japan . |

OTHER PUBLICATIONS

Keiichi Nito et al, TRT–driven Monostable Ferroelectric Liquid Crystal with Wide Viewing Angle and Fast Response Times, SID '94 Preprint, 1994.

Gorecka et al, Molecular Orientational Structures in Ferroelectric, Ferrielectric and Antiferroelectric Smectic Liquid Crystal Phases as as Studied by Conoscope Observation, Jap. Journal of Applied Physice, vol. 29, No. 1, pp. L131–137, 1990.

Funfschilling et al, Physics and Electronic Model of Deformed Helix Ferroelectric Liquid Crystal Displays, Jap. Jrnl.of App. Phy. vol. 33, p. 4950, 1994.

Okabe et al, Reentrant Antiferroelectric Phas in 4–(1–Methylheptyloxcarbon) phenyl 4'–Octylbiphenyl–4–Carboxylate, Jap. Jrnl. of App. Phy., vol. 31, p. 793, 1992.

Taniguchi, Hiroki et al, "Effect of molecular structure of core on ferroelectricity in ferroelectric liquid crystals", Jpn. J. Appl. Phys., Part 1 (1988), 27(4), 452–5 Coden: JAPNDE, 1988.

Primary Examiner—Shean C. Wu
Attorney, Agent, or Firm—Sherman and Shalloway

[57] ABSTRACT

A ferrielectric liquid crystal compound of the following general formula (1),

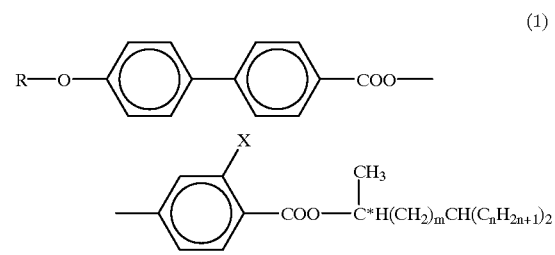

(1)

wherein R is a linear alkyl group having 6 to 12 carbon atoms; X is a hydrogen atom or a fluorine atom; m and n are the same or different from each other, each being an integer of 1 to 3; and C* is an asymmetric carbon atom, the ferrielectric liquid crystal compound being remarkably valuable as a raw material for a liquid crystal display device since it shows a ferrielectric phase in a broad temperature range and shows a high-speed response in spite of its small spontaneous polarization.

20 Claims, 1 Drawing Sheet

○ : UP STATE ON THE PLANE
⊗ : DOWN STATE ON THE PLANE

FERRIELECTRIC LIQUID CRYSTAL COMPOUND

FIELD OF THE INVENTION

The present invention relates to a novel ferrielectric liquid crystal compound suitable for use in an active matrix-type liquid crystal display device in which each pixel is individually driven by thin film transistor or metal insulator metal.

PRIOR ART

A liquid crystal display device (LCD) as a flat panel display has been already superseding a conventional display using a Braun tube, mainly in the field of portable machines and equipments. Along with the recent functional expansion of personal computers and word processors and with the recent increase in the capacity of data processing, LCD is also required to have its functions improved, that is, to have a large display capacity, full-color display, a wide viewing angle, a high-speed response and a high contrast.

As a liquid crystal display method (liquid crystal driving method) to comply with such requirements, there is proposed and practically used an active matrix (AM) display device which works by a method in which thin film transistors (TFT) or diodes (MIM) are formed such that one transistor or diode corresponds to one pixel on a display screen and a liquid crystal is driven for one pixel independently of another.

The above AM display method has problems in that it is difficult to decrease a cost due to a low yield and that it is difficult to form a large display screen. Due to a high display quality, however, the above display method is about to surpass an STN display method which has been a conventional mainstream and to overtake CRT.

Problems to be Solved by the Invention

However, the above AM display device has the following problems due to the use of a TN (twisted nematic) liquid crystal compound as a liquid crystal material.

(1) A TN liquid crystal compound is a nematic liquid crystal, and the response speed is generally low (several tens ms). In the display of video frames, no good picture quality can be obtained.

(2) A twisted state (twist alignment) of liquid crystal molecules is used for displaying, and the viewing angle is therefore narrow. In the display with a gray scale in particular, the viewing angle is sharply narrowed. That is, the contrast ratio and the color change depending upon viewing angles to a display screen.

For overcoming the above problems, in recent years, there have been proposed AM panels which use a ferroelectric liquid crystal compound or an anti-ferroelectric liquid crystal compound in place of the TN liquid crystal (Japanese Laid-open Patent Publications Nos. 249502/1993, 150257/1993 and 95080/1994). However, the following problems remain to solve for the practical use of these liquid crystal compounds.

(A) A ferroelectric liquid crystal has spontaneous polarization. An image sticking is liable to occur due to constant presence of the spontaneous polarization, and the driving is made difficult. In the display with a ferroelectric liquid crystal compound in a surface-stabilized mode, it is very difficult to perform a gray-scale display since only a bistate of black and white is possible in principle. For the gray-scale display, a special devising is required (e.g., ferroelectric liquid crystal device using monostability; Keiichi NITO et al., SID '94, Preprint, p. 48), and it is required to develop a very high technique for practical use.

(B) An anti-ferroelectric liquid crystal compound is free from the image sticking problem described in the above (1) since it has no permanent spontaneous polarization. However, the AM driving requires a liquid crystal material which can be at least driven at 10 V or less. But, the anti-ferroelectric liquid crystal generally shows a high threshold voltage, and its driving at a low voltage is therefore difficult. Further, it has a problem that the gray-scale display is difficult to perform since its optical response involves a hysteresis.

It is an object of the present invention to provide a novel material which can overcome the above problems and is suitable for use with AM driving, and a liquid crystal compound having a ferrielectric phase is thinkable as the above novel material.

A ferrielectric liquid crystal compound having a ferrielectric phase (Scγ* phase) was found for the first time in 4-(1-methylheptyloxycarbonyl)phenyl 4-(4'-octyloxybiphenyl)carboxylate (called "MHPOBC" for short) in 1989 (Japanese Journal of Applied Physics, Vol. 29, No. 1, 1990, pp. L131–137).

The structural formula and phase transition temperatures (°C.) of the MHPOBC are as follows.

Structural Formula

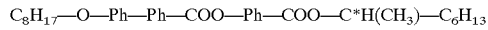

wherein Ph is a 1,4-phenylne group and C* is an asymmetric carbon atom.

Phase Sequence

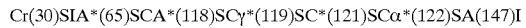

wherein Cr is a crystal phase, SIA* is a chiral smectic IA phase, SCA* is a chiral smectic CA phase (anti-ferroelectric phase), SCγ* is a chiral smectic Cγ phase (ferrielectric phase), SC* is a chiral smectic C phase (ferroelectric phase), SCα* is a chiral smectic Cα phase, SA is a smectic A phase, and I is an isotropic phase.

BRIEF DESCRIPTION OF DRAWINGS

To explain a ferrielectric liquid crystal, FIG. 1 shows molecular arrangement states of a ferrielectric phase, and FIG. 2 shows an optical response of a ferrielectric phase to a triangular wave.

Figure 1:
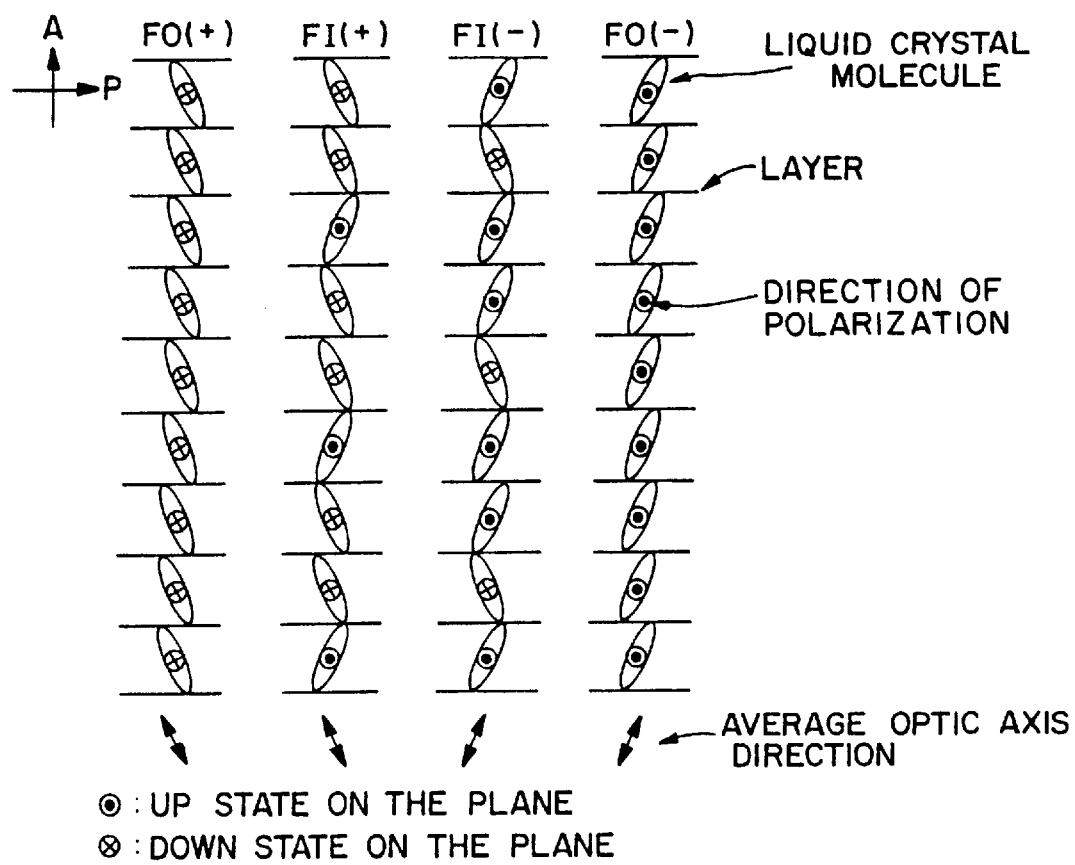
FIG. 1 shows a molecular arrangement state of a ferrielectric phase. FI(+) and FI(−) show a ferrielectric state, and FO(+) and FO(−) show an anti-ferroelectric state.

A ferrielectric phase has a molecular arrangement of FI(+) (a case where a charged voltage is positive) or a molecular arrangement state of FI(−) (a case where a charged voltage is negative) as shown in FIG. 1. In a state free of an electric field, FI(+) and FI(−) are equivalent and are therefore co-present. Therefore, average optic axes are in the direction of a layer normal, and the state free of an electric field is in a dark state under the condition of a polarizer shown in FIG. 1. This state corresponds to a portion showing a charged voltage of 0 in FIG. 2.

Further, each of FI(+) and FI(−) has spontaneous polarization as is clearly shown by the molecular arrangement states, while the spontaneous polarizations are cancelled in a state in which these are co-present. As a result, an average spontaneous polarization is zero. This shows that, like an anti-ferroelectric liquid crystal compound, a ferrielectric liquid crystal is free from an image sticking phenomenon found in a ferroelectric liquid crystal compound.

When a voltage applied to a ferrielectric liquid crystal compound is increased, a region (domain) having an extinction position appears at a voltage lower than a voltage at which a ferroelectric phase is reached. This shows that the above domain has an optic axis in the direction which tilts from the direction of layer normal although the tilt is not so large as that in a ferroelectric state.

The above intermediate state is considered either FI(+) or FI(−).

In the present invention, a liquid crystal phase which always shows the above intermediate state is called a ferrielectric phase, and a liquid crystal compound having the broadest ferrielectric phase in the phase sequence is called a ferrielectric liquid crystal compound.

Figure 2:
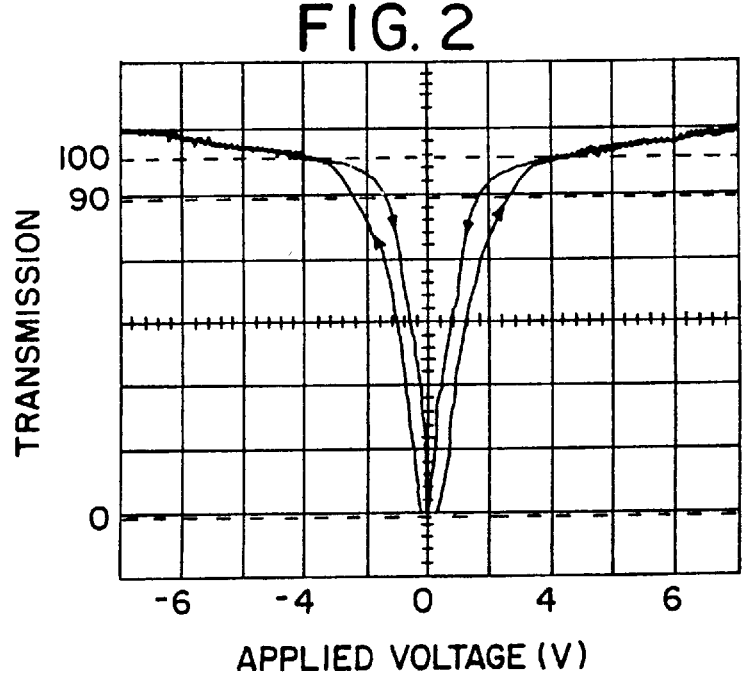
FIG. 2 shows an optical response of a ferrielectric phase to a triangular wave voltage.

When the charged voltage is further increased, the ferrielectric phase causes a phase transition to a stable ferroelectric phase FO(+) or FO(−) depending upon a direction of the electric field. That is, a portion in which the transmitted-light intensity is brought into a saturated state (flat portions on left and right sides) in FIG. 2 is FO(+) or FO(−).

In the above ferroelectric state FO(+) or FO(−), there is exhibited a spontaneous polarization greater than that in the ferrielectric phase FI(+) or FI(−) as is seen in FIG. 1. The response speed increases with an increase in the spontaneous polarization, and as a result, the capability of high response is materialized.

Both the feroelectric states are in a light state under the condition of a polarizer shown in FIG. 1.

A conventional ferroelectric liquid crystal compound provides a switching between FO(+) and FO(−), while the ferrielectric phase has a great characteristic feature in switching among four states of FO(+), FI(+), FI(−) and FO(−).

In the ferrielectric phase, therefore, not a continuous change in the intensity of transmitted light between voltages of 0 V and 4 V but a stepwise change in the intensity of transmitted light ought to be observed.

In FIG. 2, however, a continuous change in the intensity of transmitted light is observed.

It is assumed that the above occurs because the phase transition voltage from the co-presence state of FI(+) and FI(−) to FO(+) via FI(+) or the phase transition voltage from the co-presence state of FI(+) and FI(−) to FO(−) via FI(−) is not clear.

As shown in FIG. 2, generally, a ferrielectric liquid crystal compound is highly liable to show a small difference between the voltage at which it changes from a ferrielectric state to an anti-ferroelectric state and the voltage at which it changes from an anti-ferroelectric state to a ferrielectric state, that is, the width of its hysteresis tends to be very narrow. It characteristically shows a V-letter-shaped optical response and therefore has properties suitable for AM driving and a display with a gray scale in AM driving.

Further, in the change of the ferrielectric liquid crystal compound on the basis of a voltage, the voltage required for a change from a ferrielectric state to a ferroelectric state tends to be very small as compared with that of an anti-ferroelectric liquid crystal compound, and it can be therefore said that the ferrielectric liquid crystal compound is suitable for AM driving.

In the ferrielectric phase, generally, the change between the co-presence state of FI(+) and FI(−) and a ferroelectric state (FO(+) or FO(−)) is continuous, and the voltage required for the change is small. Further, the light transmittance in the co-presence state of FI(+) and FI(−) at a charged voltage of 0 can be decreased by devising an alignment film.

On the basis of these, in the ferrielectric liquid crystal compound, the co-presence state of FI(+) and FI(−) can be used as dark, the ferroelectric states FO(+) and FO(−) as light and an intermediate state of these as gray. The display principle thereof uses birefringence of a liquid crystal, and a display device having a decreased viewing angle dependency can be produced.

However, the number of ferrielectric liquid crystal compounds that have been synthesized so far is very small, and when application to an AM driving device is taken into account, few ferrielectric liquid crystal compounds that have been already known are satisfactory in respect of hysteresis and a voltage in the transition from a ferrielectric phase to a ferroelectric phase (phase transition voltage).

Further, in the active matrix driving device, it is an essential problem in practice how large or small the spontaneous polarization of the ferrielectric liquid crystal compound is.

J. Funfscilling et al show that the degree of the voltage required for driving a liquid crystal having spontaneous polarization is in proportion to the spontaneous polarization (Jpn. J. Appl. Phy. Vol. 33 pp. 4950 (1994)). It is desirable from the aspect of driving voltage that the spontaneous polarization is as small as possible. On the other hand, it is thought that the speed (response speed) in the transition from a ferrielectric state to a ferroelectric state is largely in proportion to the degree of spontaneous polarization.

It is therefore very advantageous in practice if there can be provided a ferrielectric liquid crystal compound having a small spontaneous polarization and having a high response speed.

Means to Solve the Problems

That is, the present invention is a ferrielectric liquid crystal compound of the following general formula (1),

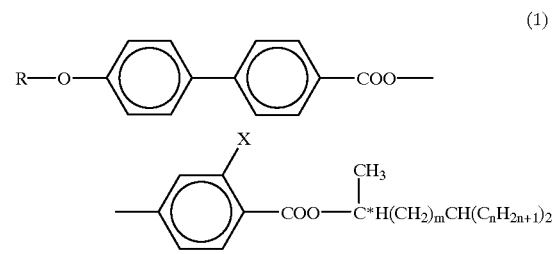

wherein R is a linear alkyl group having 6 to 12 carbon atoms; X is a hydrogen atom or a fluorine atom; m and n are the same or different from each other, each being an integer of 1 to 3; and C* is an asymmetric carbon atom.

In the above general formula (1) in the present invention, R is a linear alkyl group having 6 to 12 carbon atoms, and it is preferably a linear alkyl group having 9 to 11 carbon atoms in view of the voltage in the transition from a ferrielectric state to a ferroelectric state, the temperature range of the ferrielectric phase and the spontaneous polarization.

Further, each of m and n is independently an integer of 1 to 3. Preferably, m is 2 and n is 1. X is a hydrogen or fluorine atom, and it is preferably a fluorine atom.

When the ferrielectric compound of the present invention is considered as a raw material for practical use, the temperature (transition temperature on the high-temperature side) required for the transition from an isotropic phase, a smectic A phase or a chiral smectic C phase to a ferrielectric phase is preferably at least 40° C. On the other hand, the temperature range of the ferrielectric phase is preferably at least 50° C. from the practical point of view. That is, preferably, the difference between the transition temperature of the ferrielectric phase on the high-temperature side and the transition temperature on the low-temperature side is at least 50° C.

The voltage in the transition from a ferrielectric state to a ferroelectric state is a driving voltage, and in view of the withstanding degree of driving IC used currently, it is preferably 5 V/μm or less, more preferably 3 V/μm or less.

In the ferrielectric liquid crystal compound of the present invention, the difference between the voltage for a change from a ferrielectric state to a ferroelectric state and the voltage for a change from a ferroelectric state to a ferrielectric state is preferably 0.5 V or less.

The ferrielectric liquid crystal compound of the present invention can form an active matrix liquid crystal display device by being placed between substrates on which non-linear active devices such as thin film transistors or diodes are provided for individual pixels.

An optically active alcohol used for the synthesis of the compound of the present invention can be easily produced by the method which the present inventors have already found.

The method of the production thereof, for example, when m is 2 and n is 1, is outlined as follows.

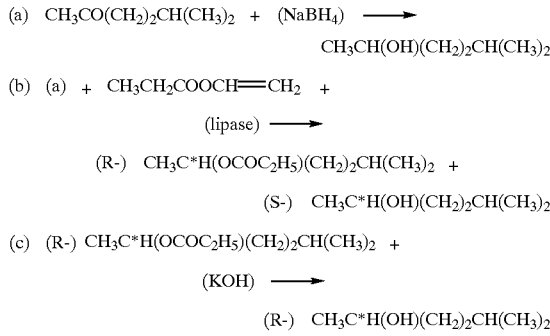

The above method of the production of the optically active alcohol will be briefly explained as follows.
(a) shows the reduction of 5-methyl-2-hexanone to an alcohol.
(b) shows an asymmetric trans-esterification in which the alcohol and vinyl propionate are caused to react in the presence of lipase.
(c) shows the hydrolysis of R-configuration ester obtained by optical resolution.

Effect of the Invention

The novel ferrielectric liquid crystal compound provided by the present invention exhibits a ferrielectric phase in a broad temperature range, and also exhibits a fast response despite having a small spontaneous polarization. Thus, the ferrielectric liquid crystal compound of the present invention is very useful as a practical raw material for a liquid crystal display device.

EXAMPLES

The present invention will be explained in more detail with reference to Examples hereinafter, while the present invention shall not be limited thereto.

Example 1

Formula (1)

$R=C_9H_{19}, X=F, m=2, n=1$ (E1)

Preparation of R-(−)-3-fluoro-4-(1,4-dimethylpentyloxycarbonyl)phenyl 4'-n-nonyloxybiphenyl-4-carboxylate (1) Preparation of 4-(4'-n-nonyloxy)biphenylcarboxylic acid 10.0 Grams of 4-(4'-hydroxy)biphenylcarboxylic acid and 14.0 g of n-nonyl bromide were added to a mixture containing 1,500 ml (milliliters) of ethanol and 200 ml of water and the mixture was reacted under reflux for 10 hours. 500 Milliliters of water was further added thereto, and the mixture was stirred for 3 hours. After completion of the reaction, the reaction mixture was acidified by adding concentrated hydrochloric acid. 500 ml of the solvent was distilled off, and the residue was cooled to room temperature to give a white solid.

The white solid was fully washed with water and then re-crystallized from chloroform to give 11.0 g of an intended product in the form of a white crystal.

(2) Preparation of 4-acetoxy-2-fluorobenzoic acid 4.3 Grams of 2-fluoro-4-hydroxybenzoic acid and 8.4 g of acetic anhydride were placed in a two-necked flask and mixed. With the mixture cooling with water, 5 drops of sulfuric acid were added. After heat generation finished, the mixture was heated at 80° C. for 30 minutes. Thereafter, the reaction mixture was poured into ice water, and a precipitated crystal was recovered by filtration.

The crystal was dried in vacuum, and used in the next step.

(3) Preparation of R-(−)-4-acetoxy-2-fluoro-1-(1,4-dimethylpentyloxycarbonyl)benzene 1.0 Gram of 4-acetoxy-2-fluorobenzoic acid was added to 7 ml of thionyl chloride, and the mixture was allowed to react under reflux for 5 hours. Then, excessive thionyl chloride was distilled off, and a mixture containing 1 ml of pyridine, 4 ml of dry ether and 0.5 g of R-(−)-5-methylhexane-2-ol was added dropwise. After the addition, the mixture was stirred at room temperature for one day and diluted with 200 ml of ether, and an organic layer was washed with diluted hydrochloric acid, with a 1N sodium hydroxide aqueous solution and with water in this order, and then dried over magnesium sulfate.

The solvent was distilled off, and the resultant crude product was purified by silica gel column chromatography using hexane/ethyl acetate as a solvent, to give an end product.

(4) Preparation of R-(−)-4-hydroxy-2-fluoro-1-(1,4dimethylpentyloxycarbonyl)benzene 1.0 Gram of the compound obtained in the above (3) was dissolved in 30 ml of ethanol, and 3 g of benzylamine was added dropwise thereto. Further, the mixture was stirred at room temperature for one day, diluted with 300 ml of ether, washed with diluted hydrochloric acid and then with water, and dried over magnesium sulfate.

The solvent was distilled off, and the remainder was subjected to silica gel column chromatography for isolation and purification to give an end product.

(5) Preparation of R-(−)-3-fluoro-4-(1,4-dimethylpentyloxycarbonyl)phenyl 4'-n-nonyloxybipheyl-4-carboxylate To 1.0 g of the compound obtained in the above (1) was added 10 ml of thionyl chloride, and the mixture was stirred under reflux for 10 hours. Excessive thionyl chloride was distilled off, and 10 ml of pyridine and 25 ml of toluene were added to the mixture. Then, 25 ml of a benzene solution containing 0.8 g of the compound obtained in the above (4) was added dropwise, and the mixture was allowed to react at room temperature for 10 hours.

After completion of the reaction, the reaction mixture was diluted with 300 ml of ether and washed with diluted hydrochloric acid, with a 1N sodium carbonate aqueous solution, and with water in this order, and an organic layer was dried over magnesium sulfate. Then, the solvent was distilled off, the remainder was isolated by silica gel column chromatography, and ethanol was used for recrystallization, to give an end product.

Example 2

Formula (1)

$R=C_{10}H_{21}, X=F, m=2, n=1$ (E2)

Preparation of R-(-)-3-fluoro-4-(1,4-dimethylpentyloxycarbonyl)phenyl 4'-n-decyloxybiphenyl-4-carboxylate Example 3

Formula (1)

$R=C_{11}H_{23}, X=F, m=2, n=1$ (E3)

Preparation of R-(-)-3-fluoro-4-(1,4-dimethylpentyloxycarbonyl)phenyl 4'-n-undecyloxybiphenyl-4-carboxylate End products were obtained in the same manner as in Example 1 except for the use of 4-(4'-n-decyloxy) biphenylcarboxylic acid (Example 2) or 4-(4'-n-undecyloxy) biphenylcarboxylic acid (Example 3) which was prepared in the same manner as in the (1) of Example 1 except that the n-nonyl bromide was replaced with n-decyl bromide (Example 2) or n-undecyl bromide (Example 3).

Example 4

Formula (1)

$R=C_9H_{19}, X=H, m=2, n=1$ (E4)

Preparation of R-(-)-4-(1,4-dimethylpentyloxycarbonyl) phenyl 4'-n-nonyloxybiphenyl-4-carboxylate An end product was obtained in the same manner as in Example 1 except for the use of 4-acetoxybenzoic acid which was prepared in the same manner as in the (2) of Example 1 except that the 4-hdyroxy-2-fluorobenzoic acid was replaced with 4-hydroxybenzoic acid.

Example 5

Formula (1)

$R=C_9H_{19}, X=H, m=3, n=1$ (E5)

Preparation of R-(-)-4-(1,5-dimethylhexyloxycarbonyl) phenyl 4'-n-nonyloxybiphenyl-4-carboxylate An end product was obtained in the same manner as in Example 1 except for the use of 4-acetoxybenzoic acid, which was prepared in the same manner as in the (2) of Example 1 except that the 4-hydroxy-2-fluorobenzoic acid was replaced with 4-acetoxybenzoic acid produced, and R-(-)-4-acetoxy-2-fluoro-1-(1,5-dimethyloxycarbonyl) benzene, which was prepared in the same manner as in the (3) of Example 1 except that the R-(-)-5-methylhexan-2-ol was replaced with R-(-)-6-methylheptane-2-ol.

Example 6

Formula (1)

$R=C_9H_{19}, X=F, m=2, n=2$ (E6)

Preparation of R-(-)-3-fluoro-4-(1-methyl-4-ethylhexyloxycarbonyl)phenyl 4'-n-nonyloxybiphenyl-4-carboxylate An end product was obtained in the same manner as in Example 1 except for the use of R-(-)-4-acetoxy-2-fluoro-1-(1-methyl-4-ethylhexyloxycarbonyl)benzene which was prepared in the same manner as in the (3) of Example 1 except that the R-(-)-5-methylhexan-2-ol was replaced with R-(-)-5-ethylhepatan-2-ol.

Table 1 shows $^1$H-NMR spectrum data of the end products obtained in the above Examples. The following formula (a) shows a chemical structure showing hydrogen atom numbers in $^1$H-NMR spectrum.

Liquid crystal phases were identified as follows. The compounds were identified for liquid crystal phases by texture observation, conoscopic image observation and DSC (differential scanning calorimeter) measurement. The observation of a conoscopic image is an effective means for identifying a ferrielectric phase. The conoscopic image observation was conducted according to a literature (J. Appl. Phys. 31, 793 (1992)).

The texture observation based on general parallel alignment cells, the conoscopic observation and the DSC measurement showed that the compounds of the present invention had phase sequences shown in Table 2 and were ferrielectric liquid crystal compounds.

Then, the obtained ferrielectric liquid crystal compounds were measured for optical responses.

Cells were prepared by the following procedures.

A pair of glass plates with insulating film ($SiO_2$, thickness; 50 nm) and ITO electrodes were coated with polyimide (thickness; about 80 nm), and one of the glass plates was rubbed.

The glass plates were attached to each other through a spacer having a particle diameter of 1.6 μm to form a test cell. The cell had a thickness of 2 μm.

A liquid crystal compound was heated until the liquid crystal showed an isotropic phase and then, the liquid crystal was injected into the test cell by capillarity. Then, the cell was gradually cooled at a rate of 1° C./minute to align the liquid crystal in parallel.

The light transmittance was defined as follows. A lowest intensity of transmitted light was 0% of light transmittance, and a highest intensity of transmitted light was 100% of light transmittance.

The phase transfer voltage was defined to be a voltage found at a light transmittance of 90%. A triangular wave voltage of ±10 V, 5 Hz was applied to the test cell, and a voltage in the transition from a ferrielectric phase to a ferroelectric phase was determined at 50° C.

The spontaneous polarization was determined by applying a triangular wave voltage of 10 V at 50° C. and measuring a polarization inversion voltage.

The response speed was defined to be a time period required for a change from 0% to 90% in the light transmittance, and it was measured at 50° C. by applying a rectangular wave voltage of 8V, 10 Hz.

Table 2 shows the results.

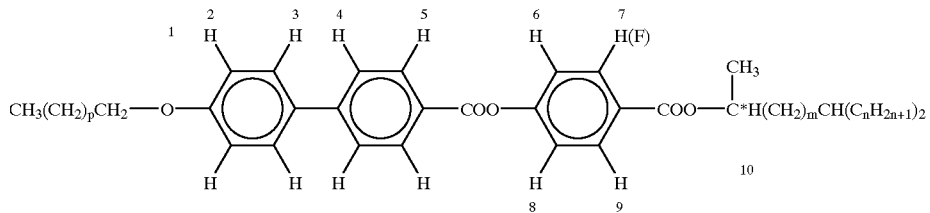

(a)

In the above formula

Example 1 (E1): p = 7 m= 2 n = 1 X = F
Example 2 (E2): p = 8 m= 2 n = 1 X = F
Example 3 (E3): p = 9 m= 2 n = 1 X = F
Example 4 (E4): p = 7 m= 2 n = 1 X = H
Example 5 (E5): p = 7 m= 3 n = 1 X = H
Example 6 (E6): p = 7 m= 2 n = 2 X = H

TABLE 1

| Hydrogen atom number | Chemical shift (ppm) | | | | | | | | | |
|---|---|---|---|---|---|---|---|---|---|---|
| | 1 | 2 | 3 | 4 | 5 | 6 | 7 | 8 | 9 | 10 |
| Example.1 (E1) | 4.0 | 7.0 | 7.6 | 7.7 | 8.2 | 7.1 | | 7.1 | 8.0 | 5.2 |
| Example.2 (E2) | 4.0 | 7.0 | 7.6 | 7.7 | 8.2 | 7.1 | | 7.1 | 8.0 | 5.1 |
| Example.3 (E3) | 4.0 | 7.0 | 7.6 | 7.7 | 8.2 | 7.1 | | 7.1 | 8.0 | 5.1 |
| Example.4 (E4) | 4.0 | 7.0 | 7.6 | 7.7 | 8.2 | 7.3 | 8.1 | 7.3 | 8.1 | 5.2 |
| Example.5 (E5) | 4.0 | 7.0 | 7.6 | 7.7 | 8.2 | 7.3 | 8.1 | 7.3 | 8.3 | 5.2 |
| Example.6 (E6) | 4.0 | 7.0 | 7.6 | 7.7 | 8.2 | 7.1 | | 7.1 | 8.0 | 5.2 |

TABLE 2

| | Phase sequence | Phase transition voltage (V/$\mu$m) | Response time ($\mu$ second) | Spontaneous polarization (nC/cm$^2$) | Melting point (° C.) |
|---|---|---|---|---|---|
| Example.1 (E1) | I (139) SA (128) SC$\gamma$* (27) Cr | 2.3 | 84 | 103 | 70 |
| Example.2 (E2) | I (133) SA (123) SC$\gamma$* (58) Cr | 1.5 | 255 | 106 | 45 |
| Example.3 (E3) | I (133) SA (123) SC$\gamma$* (−1) Cr | 1.7 | 255 | 91 | 60 |
| Example.4 (E4) | I (143) SA (127) SC$\gamma$* (68) Cr | 2.0[*1] | 27[*1] | 149[*1] | 99 |
| Example.5 (E5) | I (138) SA (122) SC$\gamma$* (50) Cr | 1.7[*1] | 23[*1] | 158[*1] | 95 |
| Example.6 (E6) | I (118) SA (110) SC$\gamma$* (−8) Cr | 2.2 | 404 | 135 | 70 |

What is claimed is:

1. A ferrielectric liquid crystal compound represented by the following general formula (1),

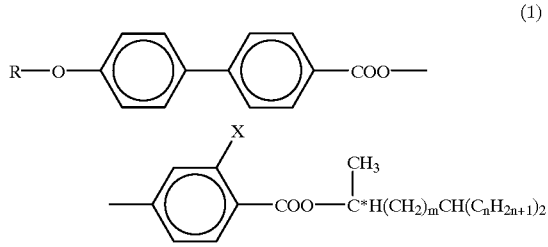

(1)

wherein R is a linear alkyl group having 6 to 12 carbon atoms; X is a hydrogen atom or a fluorine atom; m and n are the same or different from each other, each being an integer of 1 to 3; and C* is an asymmetric carbon atom.

2. The ferrielectric liquid crystal compound of claim 1, wherein, in the general formula (1), m is 2 and n is 1.

3. The ferrielectric liquid crystal compound of claim 1, wherein, in the general formula (1), X is a fluorine atom.

4. The ferrielectric liquid crystal compound of claim 1, wherein, in the general formula (1), R is a linear alkyl group having 9 to 11 carbon atoms.

5. The ferrielectric liquid crystal compound of claim 1, wherein a difference between a phase transition temperature of a ferrielectric phase on a high-temperature side and a phase transition temperature of the ferrielectric phase on a low-temperature side is at least 50° C.

6. The ferrielectric liquid crystal compound of claim 1, wherein a voltage in transition from a ferrielectric state to a ferroelectric state is 5 V/$\mu$m or less.

7. The ferrielectric liquid crystal compound of claim 1, wherein a voltage in transition from a ferrielectric state to a ferroelectric state is 3 V/$\mu$m or less.

8. The ferrielectric liquid crystal compound of claim 1, which has functions to switch to a co-presence state of two ferrielectric phases, to two ferroelectric phases and to an intermediate state between them by changing the voltage.

9. The ferrielectric liquid crystal compound of claim 1, wherein a difference between a voltage for a change from a ferrielectric phase to a ferroelectric state and a voltage for a change from a ferroelectric state to a ferrielectric state is 0.5 V or less.

10. An active-matrix liquid crystal display device comprising the ferrielectric liquid crystal compound of claim 1, which is interposed between substrates on which non-linear active devices of thin film transistors or diodes are provided for individual pixels.

11. A ferrielectric phase liquid crystal compound represented by the following general formula (1),

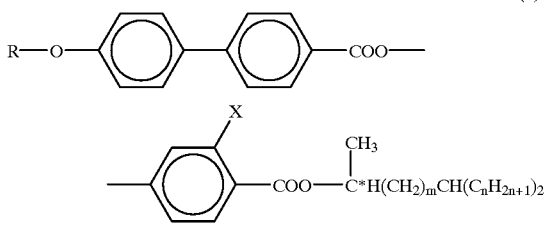

(1)

wherein R is linear alkyl group having 9 to 11 carbon atoms; X is a hydrogen atom or a fluorine atom; m is 2 or 3 and n is 1 or 2; and C* is an asymmetric carbon atom.

12. The ferrielectric phase liquid crystal compound of claim 11, wherein, in the general formula (1), R is 9, m is 2, n is 1 and X is fluorine atom.

13. The ferrielectric phase liquid crystal compound of claim 11, wherein, in the general formula (1), R is 10, m is 2, n is 1 and X is a fluorine atom.

14. The ferrielectric phase liquid crystal compound of claim 11, wherein, in the general formula (1), R is 11, m is 2, n is 1 and X is fluorine atom.

15. The ferrielectric phase liquid crystal compound of claim 11, wherein, in the general formula (1), R is 9, m is 2, n is 1 and X is hydrogen atom.

16. The ferrielectric phase liquid crystal compound of claim 11, wherein, in the general formula (1), R is 9, m is 3, n is 1 and X is hydrogen atom.

17. The ferrielectric phase liquid crystal compound of claim 11, wherein, in the general formula (1), R is 9, m is 2, n is 2 and X is fluorine atom.

18. The ferrielectric liquid crystal compound of claim 11, wherein a difference between a phase transition temperature of a ferrielectric phase on a high-temperature side and a phase transition temperature of the ferrielectric phase on a low-temperature side is at least 50° C.

19. The ferrielectric liquid crystal compound of claim 11, wherein a voltage in transition from a ferrielectric state to a ferroelectric state is 5 V/μm or less.

20. The ferrielectric liquid crystal compound of claim 11, wherein a voltage in transition from a ferrielectric state to a ferroelectric state is 3 V/μm or less.

* * * * *